United States Patent
Baharaff et al.

(10) Patent No.: US 12,239,712 B2
(45) Date of Patent: Mar. 4, 2025

(54) COMBINATION THERAPY FOR THE TREATMENT OF LIVER DISEASE

(71) Applicant: GALMED RESEARCH AND DEVELOPMENT LTD, Tel Aviv (IL)

(72) Inventors: Allen Baharaff, Tel Aviv (IL); Liat Hayardany-Nissimov, Tel Aviv (IL); Tali Gorfine, Tel Aviv (IL)

(73) Assignee: GALMED RESEARCH AND DEVELOPMENT LTD, Tel Aviv (IL)

( * ) Notice: Subject to any disclaimer, the term of this patent is extended or adjusted under 35 U.S.C. 154(b) by 1032 days.

(21) Appl. No.: 17/273,318

(22) PCT Filed: Sep. 3, 2019

(86) PCT No.: PCT/IL2019/050983
§ 371 (c)(1),
(2) Date: Mar. 4, 2021

(87) PCT Pub. No.: WO2020/049556
PCT Pub. Date: Mar. 12, 2020

(65) Prior Publication Data
US 2021/0338826 A1 Nov. 4, 2021

Related U.S. Application Data

(60) Provisional application No. 62/727,565, filed on Sep. 6, 2018.

(51) Int. Cl.
*A61K 31/192* (2006.01)
*A61K 31/53* (2006.01)
*A61K 31/575* (2006.01)
*A61K 31/665* (2006.01)
*A61K 47/54* (2017.01)
*A61P 1/16* (2006.01)

(52) U.S. Cl.
CPC .......... *A61K 47/554* (2017.08); *A61K 31/192* (2013.01); *A61K 31/53* (2013.01); *A61K 31/575* (2013.01); *A61K 31/665* (2013.01); *A61P 1/16* (2018.01)

(58) Field of Classification Search
CPC .... A61K 31/53; A61K 31/192; A61K 47/554; A61P 1/16
See application file for complete search history.

(56) References Cited

U.S. PATENT DOCUMENTS

2018/0125862 A1* 5/2018 Hayardeny-Nissimov ................ A61K 45/06

FOREIGN PATENT DOCUMENTS

| CN | 101228135 | 7/2008 |
| WO | WO 2007/009913 A1 | 1/2007 |
| WO | WO 2018/075650 A1 | 4/2018 |

OTHER PUBLICATIONS

Friedman et. al (Thyroid hormone receptor agonist improves liver fat, lipoproteins in NASH (2017)). (Year: 2017).*
Safadi et. al. (Clinical Gastroenterology and Hepatology (2014) 12:2085-2091). (Year: 2014).*
Bennett "Thyroid hormone receptor agonist improves liver fat, lipoproteins in NASH", Healio, Dec. 7, 2017, 2pp; Retrieved from the Internet:URL:https://www.healio.com/hepatology/steatohepatitis-metabolic-liver-disease/news/online/{7b591f60-56e0-4eb7-984d-1cd194f90074}/thyroid hormone-receptor-agonist-improves-liver-fat-lipoproteins-in-nash; retrieved on May 8, 2020.
Farrell et al. "Nonalcoholic fatty liver disease: from steatosis to cirrhosis" Hepatology. Feb. 2006;43(S1):S99-112.
Gilat et al. "Prevention of diet-induced fatty liver in experimental animals by the oral administration of a fatty acid bile acid conjugate (FABAC)" Hepatology. Aug. 1, 2003:38(2):436-42.
International Search Report for PCT Application No. PCT/IL2019/050983 dated Oct. 23, 2019.
Kowalik et al. "Thyroid hormones, thyromimetics and their metabolites in the treatment of liver disease" Frontiers in endocrinology. Jul. 10, 2018;9:382.
Palekar et al. "Clinical model for distinguishing nonalcoholic steatohepatitis from simple steatosis in patients with nonalcoholic fatty liver disease" Liver International. Mar. 2006;26(2):151-6.
Safadi et al. "The fatty acid-bile acid conjugate aramchol reduces liver fat content in patients with nonalcoholic fatty liver disease" Clinical Gastroenterology and Hepatology. Dec. 1, 2014;12(12):2085-91.
Supplementary European Search Report for European Application No. 19858453.4 dated Apr. 26, 2022.

* cited by examiner

*Primary Examiner* — Marcos L Sznaidman
(74) *Attorney, Agent, or Firm* — Mark Cohen; Pearl Cohen; ZEDEK LATZER BARATZ LLP

(57) ABSTRACT

The invention relates to pharmaceutical compositions, and more specifically to pharmaceutical compositions comprising at least one fatty acid-bile acid conjugate and at least one thyroid hormone receptor agonist or thyroid hormone mimetic or pharmaceutically acceptable salts thereof, and use of such compositions in methods of treating, stabilizing or lessening the severity or progression of a liver disease including fibrosis, non-alcoholic fatty liver disease (NAFLD), non-alcoholic steatohepatitis (NASH), and comorbidity ties associated with a liver disease.

16 Claims, No Drawings

COMBINATION THERAPY FOR THE TREATMENT OF LIVER DISEASE

CROSS-REFERENCE TO RELATED APPLICATIONS

This application is a National Phase Application of PCT International Application No. PCT/IL2019/050983, International Filing Date Sep. 3, 2019, claiming priority from U.S. Provisional Ser. No. 62/727,565 Patent Application, which is hereby incorporated by reference.

FIELD OF THE INVENTION

The invention relates to pharmaceutical compositions, and more specifically to pharmaceutical compositions comprising at least one fatty acid-bile acid conjugate and at least one thyroid hormone receptor agonist or thyroid hormone mimetic or pharmaceutically acceptable salts thereof, and use of such compositions in methods of treating, stabilizing or lessening the severity or progression of a liver disease including fibrosis, non-alcoholic fatty liver disease (NAFLD), non-alcoholic steatohepatitis (NASH), and comorbidities associated with a liver disease.

BACKGROUND OF THE INVENTION

Fatty liver is one of the most common liver diseases known today. It occurs due to excessive accumulation of fat in the liver. It is demonstrated histologically by the presence of variable amounts of micro and/or macro vesicular fat droplets in the liver tissue. Fatty liver can be caused by drugs, chemicals, diseases, bacteria, etc. but the main cause is excessive dietary intake leading to (mainly truncal) obesity and insulin resistance. Due to the increasing prevalence of obesity in affluent societies the prevalence of fatty liver is rising. Fatty liver may progress to steatohepatitis and cirrhosis with the attendant morbidity and mortality. The best treatment for diet-induced fatty liver is sustained weight loss. However, it is well known that this is rarely achieved.

The term nonalcoholic fatty liver disease (NAFLD) describes a spectrum of liver diseases ranging from simple fatty liver (steatosis) to nonalcoholic steatohepatitis (NASH) with progressive fibrosis and liver failure. NAFLDs exhibit the histological features of alcohol-induced liver disease in patients who do not consume significant amounts of alcohol. In NASH, the fat accumulation is associated with varying degrees of inflammation and fibrosis. All the stages of NAFLD have in common the accumulation of fat in the liver cells.

Nonalcoholic steatohepatitis (NASH) is the advanced form of nonalcoholic fatty liver disease (NAFLD) which sets the stage for further liver damage. The mechanism for the progression of NASH involves multiple parallel "hits" or insults to the system, including steatosis, oxidative stress, mitochondrial dysfunction, apoptosis, inflammation, hepatic stellate cell activation and collagen production.

Fibrosis refers to the formation of excess fibrous connective tissue in an organ or tissue in a reparative or reactive process. This can be a reactive, benign, or pathological state. The deposition of connective tissue in the organ and/or tissue can obliterate the architecture and function of the underlying organ or tissue. Fibrosis is this pathological state of excess deposition of fibrous tissue, as well as the process of connective tissue deposition in healing.

The burden of liver diseases, combined with a lack of any effective approved therapeutic interventions for NAFLDs such as NASH, represents an unmet medical need.

Background art includes U.S. Publication No. US2018/0125862A; Farrell and Larter, Hepatology, 243:S99-S112 (2006); Palekar, et al., Liver int., 26(2): 151-6 (2006).

Many patients do not respond to available treatments for fatty liver disease, and long term treatment is limited by toxicity and side effects. The development of safe and effective treatments for liver disease, including fibrosis, non-alcoholic fatty liver disease (NAFLD), non-alcoholic steatohepatitis (NASH), and comorbidities associated with a liver disease, would be highly beneficial.

SUMMARY OF THE INVENTION

In one embodiment the present invention provides a therapeutic combination of at least one fatty acid-bile acid conjugate (FABAC), or a pharmaceutically acceptable salt thereof, and at least one thyroid hormone receptor agonist or thyroid hormone mimetic, or a pharmaceutically acceptable salt thereof, and a carrier.

In another embodiment, the present invention provides a method of treating, stabilizing or lessening the severity or progression of a liver disease, comprising co-administrating to a subject in need thereof a therapeutically effective amount of at least one fatty acid-bile acid conjugate; and at least one thyroid hormone analogue or thyroid hormone receptor agonist or salts thereof.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

Embodiments of the invention relate to pharmaceutical compositions comprising at least one fatty acid-bile acid conjugate (FABAC) and at least one thyroid hormone receptor agonist or thyroid hormone mimetic or pharmaceutically acceptable salts thereof, and use of such compositions for treating, stabilizing or lessening the severity or progression of a liver disease, such as non-alcoholic fatty liver disease (NAFLD), non-alcoholic steatohepatitis (NASH), fibrosis and comorbidities thereof.

Before explaining at least one embodiment in detail, it is to be understood that the invention is not necessarily limited in its application to the details of construction and the arrangement of the components and/or methods set forth herein. The invention is capable of other embodiments or of being practiced or carried out in various ways. The phraseology and terminology employed herein are for descriptive purpose and should not be regarded as limiting.

According to an aspect of some embodiments of the present invention, there is provided a composition comprising a therapeutically effective amount of at least one fatty acid-bile acid conjugate and at least one thyroid hormone analogue or thyroid hormone receptor agonist.

In some embodiments, the at least one fatty acid-bile acid conjugate has the general formula I:

$$W-X-G;$$ (Formula I)

wherein:

G is a bile acid or bile salt radical;

W is one or two fatty acid radicals; and

X is either (i) one bonding member between the bile acid or bile salt radical and one fatty acid radical or (ii) two bonding members between two fatty acid radicals and two positions of the bile acid or bile salt radical, the bonding member(s) being —NH, —O or a direct bond.

In some embodiments, the at least one fatty acid-bile acid conjugate is 3-beta-arachidylamido-7-alpha, 1-2alpha-dihydroxy-5-beta-cholan-24-oic acid (Aramchol™).

In some embodiments, the at least one thyroid hormone analogue or thyroid hormone receptor agonist comprises a selective thyroid hormone receptor-beta agonist selected from the group consisting of

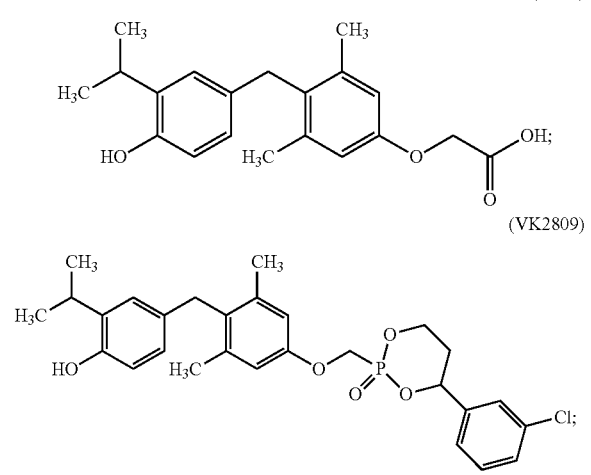

(GC-1)

(VK2809)

and a compound represented by the structure of Formula II:

(Formula II)

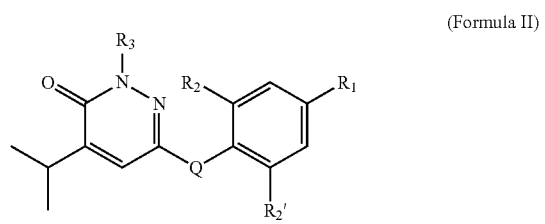

wherein:

$R_1$ is alkyl-COOH, amino acid,

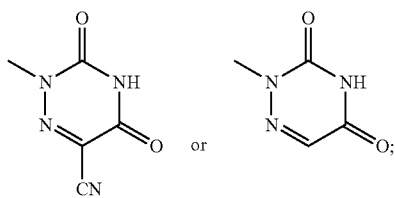

or $R_2$, $R_2'$ are independently alkyl or halide;

Q is O, alkyl, S or $SO_2$; and $R_3$ is H or alkyl;

or a pharmaceutically acceptable salts thereof, including mixtures thereof in all ratios and combination thereof.

In some embodiments, $R_1$ of Formula II is alkyl-COOH. In other embodiments, $R_1$ of Formula II is $(CH_2)n$-COOH, wherein n is between 1-6. In other embodiments, $R_1$ of Formula II is $CH_2$—COOH. In other embodiments, $R_1$ of Formula II is $CH_2$—$CH_2$—COOH. In other embodiments, $R_1$ of Formula II is $CH_2$—$CH_2$—$CH_2$—COOH. In other embodiments, $R_1$ of Formula II is $CH_2$—$CH_2$—$CH_2$—$CH_2$—COOH. In other embodiments, $R_1$ of Formula II is $CH_2$—$CH_2$—$CH_2$—$CH_2$—$CH_2$—COOH. In other embodiments, $R_1$ of Formula II is $CH_2$—$CH_2$—$CH_2$—$CH_2$—$CH_2$—$CH_2$—COOH.

In some embodiments, $R_1$ of Formula II is an amino acid, wherein the amino acid is linked by the amino acid side of the amino acid. In some embodiments, the amino acid is alanine. In other embodiments, the amino acid is arginine. In other embodiments, the amino acid is asparagine. In other embodiments, the amino acid is aspartic acid. In other embodiments, the amino acid is cycteine. In other embodiments, the amino acid is glutamic acid. In other embodiments, the amino acid is glutamine. In other embodiments, the amino acid is glycine. In other embodiments, the amino acid is histidine. In other embodiments, the amino acid is hydroxyproline. In other embodiments, the amino acid is isoleucine. In other embodiments, the amino acid is leucine. In other embodiments, the amino acid is lysine. In other embodiments, the amino acid is methionine. In other embodiments, the amino acid is phenylalanine. In other embodiments, the amino acid is proline. In other embodiments, the amino acid is pyroglutamatic acid. In other embodiments, the amino acid is serine. In other embodiments, the amino acid is threonine. In other embodiments, the amino acid is tryptophan. In other embodiments, the amino acid is tyrosine. In other embodiments, the amino acid is valine.

In some embodiments, $R_2$ is alkyl. In other embodiments, $R_2$ is halide.

In some embodiments, $R_2'$ is alkyl. In other embodiments, $R_2'$ is halide.

In some embodiments, Q is O. In other embodiments, Q is alkyl. In other embodiments, Q is S. In other embodiments, Q is $SO_2$.

In some embodiments, $R_3$ is H. in other embodiments, $R_3$ is alkyl.

In some embodiments, the at least one thyroid hormone analogue or thyroid hormone receptor agonist comprises a selective thyroid hormone receptor-beta agonist selected from the group consisting of (GC-1)

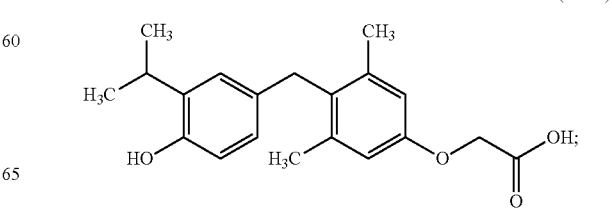

-continued

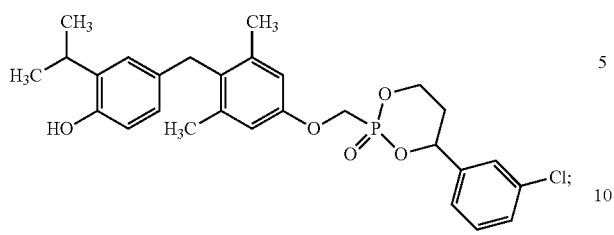
(VK2809)

and
a compound represented by the structure of Formula II:

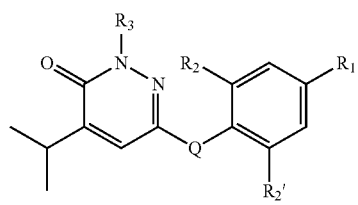
(Formula II)

wherein:

| $R_1$ | $R_2, R_2'$ | Q | $R_3$ |
| --- | --- | --- | --- |
| —CH$_2$CO$_2$H | CH$_3$, CH$_3$ | O | H |
| —CH$_2$CO$_2$H | CH$_3$, Cl | O | H |
| —CH$_2$CO$_2$H | Cl, Cl | O | H |
| —CH$_2$CO$_2$H | Br, Br | O | H |
| —CH$_2$CH$_2$CO$_2$H | Br, Br | O | H |
| —CH$_2$CO$_2$H | Cl, Cl | O | CH$_3$ |
| —NHCH$_2$CO$_2$H | Cl, Cl | O | H |
| —NHCOCO$_2$H | Cl, Cl | O | H |
| —CH$_2$CO$_2$H | Cl, Cl | —CH$_2$— | H |
| —CH$_2$CO$_2$H | Br, Br | —CH$_2$— | H |
| —CH$_2$CO$_2$H | Cl, Cl | S | H |
| —CH$_2$CO$_2$H | Cl, Cl | SO | H |
| —CH$_2$CO$_2$H | Cl, Cl | SO$_2$ | H |
| ![triazine-CN] | Cl, Cl | O | H |
| ![triazine-CN] | Cl, Cl | —CH$_2$— | H |
| ![triazine-CN] | Cl, Cl | O | CH$_3$ |
| ![triazine-CN] | Cl, Cl | —CH$_2$— | CH$_3$ |
| ![triazine] | Cl, Cl | O | H |
| ![triazine] | Cl, Cl | —CH$_2$— | H | or a pharmaceutically acceptable salts thereof, including mixtures thereof in all ratios and combination thereof.

In some embodiments, the at least one thyroid hormone analogue or thyroid hormone receptor agonist is selected from the group consisting of 2-[3,5-dichloro-4-(5-isopropyl-6-oxo-1,6-dihydropyridazin-3-yloxy) phenyl]-3,5-dioxo-2,3,4,5-tetrahydro[1,2,4] triazine-6-carbonitrile (MGL-3196), 2-[4-[[4-Hydroxy-3-(1-methylethyl)phenyl] methyl]-3,5-dimethylphenoxy] acetic acid (GC1) and 2-((3,5-dimethyl-4-(4'-hydroxy-3'-isopropylbenzyl)phenoxy)methyl)-4-(3-chlorophenyl)-2-oxido(1,3,2)dioxaphosphonane (VK2809) or combinations thereof.

In some embodiments, the at least one thyroid hormone analogue or thyroid hormone receptor agonist comprises MGL-3196. In some such embodiments, the at least one thyroid hormone analogue or thyroid hormone receptor agonist consists essentially of MGL-3196.

In some embodiments, the at least one thyroid hormone analogue or thyroid hormone receptor agonist comprises levothyroxine (L-thyroxine). In some such embodiments, the levothyroxine (L-thyroxine) comprises levothyroxine (L-thyroxine) sodium. In some embodiments, the at least one thyroid hormone analogue or thyroid hormone receptor agonist comprises dextrothyroxine. In some such embodiments, the dextrothyroxine comprises dextrothyroxine sodium. In some embodiments, the at least one thyroid hormone analogue or thyroid hormone receptor agonist comprises desiccated thyroid. In some embodiments, the at least one thyroid hormone analogue or thyroid hormone receptor agonist comprises thyroid extract. In some embodiments, the at least one thyroid hormone analogue or thyroid hormone receptor agonist comprises liothyronine. In some such embodiments, the liothyronine comprises liothyronine sodium. In some embodiments, the at least one thyroid hormone analogue or thyroid hormone receptor agonist comprises liotrix.

In some embodiments, the at least one fatty acid-bile acid conjugate comprises Aramchol™ and the at least one thyroid hormone analogue or thyroid hormone receptor agonist comprises MGL-3196. In some embodiments, the at least one fatty acid-bile acid conjugate consists essentially of Aramchol™ and the at least one thyroid hormone analogue or thyroid hormone receptor agonist consists essentially of MGL-3196.

According to an aspect of some embodiments of the present invention, there is provided a pharmaceutical composition comprising the composition disclosed herein and at least one pharmaceutically acceptable excipient.

According to an aspect of some embodiments of the present invention, there is provided a hepatically effective composition comprising the pharmaceutical composition disclosed herein, wherein said at least one fatty acid-bile acid conjugate and said at least one thyroid hormone analogue or thyroid hormone receptor agonist are present in the hepatically effective composition in a synergistically effective amount.

In some embodiments of the hepatically effective composition, administration of the synergistically effective amount provides for at least one therapeutic effect selected from the group consisting of:
a) a lower dose of at least one of the at least one fatty acid-bile acid conjugate or the at least one thyroid hormone analogue or thyroid hormone receptor agonist;
b) a shorter treatment schedule; and
c) reduced incidence or severity of side-effects,
as compared to the effect obtainable by administration of at least one compound comprising the at least one fatty acid-bile acid conjugate or the at least one thyroid hormone analogue or thyroid hormone receptor agonist in the absence of the other compound.

In some embodiments of the hepatically effective composition, the at least one fatty acid-bile acid conjugate comprises Aramchol™ and the at least one thyroid hormone analogue or thyroid hormone receptor agonist comprises MGL-3196, and the synergistically effective amount is at least one of from greater than 0 mg to less than 50 mg of MGL-3196 (such as about 0.2 mg, about 0.5 mg, about 1 mg, about 10 mg, about 20 mg, about 30 mg, about 40 mg or about 45 mg) and from greater than 0 mg to less than 400 mg of Aramchol™ (such as about 0.2 mg, about 0.5 mg, about 1 mg, about 10 mg, about 20 mg, about 30 mg, about 40 mg, about 50 mg, about 95 mg, about 100 mg, about 150 mg, about 200 mg, about 250 mg, about 300 mg, about 350 mg, or about 395 mg).

In some such embodiments, Aramchol™ is present in the composition in an amount of from greater than 0 mg to less than 300 mg.

In some such embodiments, Aramchol™ is present in the composition in an amount of from greater than 0 mg to less than 100 mg.

According to an aspect of some embodiments of the present invention, there is provided the composition as disclosed herein for use in the treatment of a liver disease.

According to an aspect of some embodiments of the present invention, there is provided the use of the composition as disclosed herein in the manufacture of a medicament for treatment of a liver disease.

In some embodiments of the composition for use or the use as disclosed herein, the liver disease is selected from the group consisting of non-alcoholic steatohepatitis (NASH), non-alcoholic fatty liver disease (NAFLD), emerging cirrhosis, non-cirrhotic hepatic fibrosis and liver fibrosis.

In some such embodiments, the liver fibrosis is associated with at least one condition selected from the group consisting of non-alcoholic fatty liver disease (NAFLD), non-alcoholic steatohepatitis (NASH) and emerging cirrhosis.

In some such embodiments, the liver fibrosis comprises non-cirrhotic hepatic fibrosis.

In some embodiments of the composition for use or the use as disclosed herein, the subject has a disease or condition selected from the group consisting of human immunodeficiency virus (HIV) infection, HIV and HCV co-infection, viral hepatitis, type 2 diabetes mellitus (T2DM), metabolic syndrome (MS), or a combination thereof.

In some such embodiments, the viral hepatitis is HBV or HCV infection.

In some embodiments of the composition for use or the use as disclosed herein, the at least one fatty acid-bile acid conjugate and the at least one thyroid hormone analogue or thyroid hormone receptor agonist are present in a synergistically effective amount.

In some such embodiments, administration of the synergistically effective amount provides for at least one therapeutic effect selected from the group consisting of:
a) a lower dose of at least one of said at least one fatty acid-bile acid conjugate or at least one thyroid hormone analogue or thyroid hormone receptor agonist;
b) a shorter treatment schedule; and
c) reduced incidence or severity of side-effects,
as compared to the effect obtainable by administration of at least one compound comprising the at least one fatty acid-bile acid conjugate or the at least one thyroid hormone analogue or thyroid hormone receptor agonist in the absence of the other compound.

In some embodiments of the composition for use or the use as disclosed herein, the at least one fatty acid-bile acid conjugate comprises Aramchol™ and the at least one thyroid hormone analogue or thyroid hormone receptor agonist comprises MGL-3196, and the synergistically effective amount is at least one of from greater than 0 mg to less than 50 mg of MGL-3196 (such as about 0.2 mg, about 0.5 mg, about 1 mg, about 10 mg, about 20 mg, about 30 mg, about 40 mg or about 45 mg) and from greater than 0 mg to less than 400 mg of Aramchol™ (such as about 0.2 mg, about 0.5 mg, about 1 mg, about 10 mg, about 20 mg, about 30 mg, about 40 mg, about 50 mg, about 95 mg, about 100 mg, about 150 mg, about 200 mg, about 250 mg, about 300 mg, about 350 mg, or about 395 mg).

In some such embodiments, Aramchol™ is present in the composition in an amount of from greater than zero mg to less than 300 mg.

In some such embodiments, Aramchol™ is present in the composition in an amount of from greater than zero mg to less than 100 mg.

According to an aspect of some embodiments of the present invention, there is provided a method of treating, stabilizing or lessening the severity or progression of a liver disease and/or comorbidities, comprising co-administering to a subject in need thereof a therapeutically effective amount of at least one fatty acid-bile acid conjugate; and at least one thyroid hormone analogue or thyroid hormone receptor agonist or salts thereof.

In some embodiments of the method disclosed herein, the at least one fatty acid-bile acid conjugate has the general formula I:

$$W\text{---}X\text{-}G \qquad \text{(Formula I)};$$

wherein:
G is a bile acid or bile salt radical;
W is one or two fatty acid radicals; and
X is either (i) one bonding member between the bile acid or bile salt radical and one fatty acid radical or (ii) two bonding members between two fatty acid radicals and two positions of the bile acid or bile salt radical, the bonding member(s) being —NH, —O or a direct bond.

In some embodiments of the method, the at least one fatty acid-bile acid conjugate is 3-beta-arachidylamido-7-alpha, 1-2alpha-dihydroxy-5-beta-cholan-24-oic acid (Aramchol™).

In some embodiments, the at least one thyroid hormone analogue or thyroid hormone receptor agonist comprises a selective thyroid hormone receptor-beta agonist selected from the group consisting of

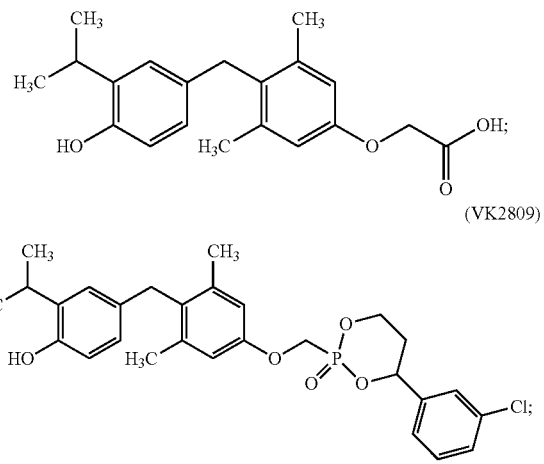

and
a compound represented by the structure of Formula II:

(Formula II)

wherein:
R$_1$ is alkyl-COOH, amino acid,

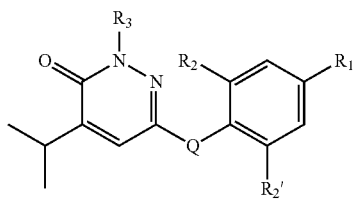

R$_2$, R$_2$' are independently alkyl or halide;
Q is O, alkyl, S or SO$_2$; and
R$_3$ is H or alkyl;
or a pharmaceutically acceptable salts thereof, including mixtures thereof in all ratios and combination thereof.

In some embodiments, R$_1$ of Formula II is alkyl-COOH. In other embodiments, R$_1$ of Formula II is (CH$_2$)n-COOH, wherein n is between 1-6. In other embodiments, R$_1$ of Formula II is CH$_2$—COOH. In other embodiments, R$_1$ of Formula II is CH$_2$—CH$_2$—COOH. In other embodiments, R$_1$ of Formula II is CH$_2$—CH$_2$—CH$_2$—COOH. In other embodiments, R$_1$ of Formula II is CH$_2$—CH$_2$—CH$_2$—CH$_2$—COOH. In other embodiments, R$_1$ of Formula II is CH$_2$—CH$_2$—CH$_2$—CH$_2$—CH$_2$—COOH. In other embodiments, R$_1$ of Formula II is CH$_2$—CH$_2$—CH$_2$—CH$_2$—CH$_2$—CH$_2$—COOH.

In some embodiments, R$_1$ of Formula II is an amino acid, wherein the amino acid is linked by the amino acid side of the amino acid. In some embodiments, the amino acid is alanine. In other embodiments, the amino acid is arginine. In other embodiments, the amino acid is asparagine. In other embodiments, the amino acid is aspartic acid. In other embodiments, the amino acid is cycteine. In other embodiments, the amino acid is glutamic acid. In other embodiments, the amino acid is glutamine. In other embodiments, the amino acid is glycine. In other embodiments, the amino acid is histidine. In other embodiments, the amino acid is hydroxyproline. In other embodiments, the amino acid is isoleucine. In other embodiments, the amino acid is leucine. In other embodiments, the amino acid is lysine. In other embodiments, the amino acid is methionine. In other embodiments, the amino acid is phenylalanine. In other embodiments, the amino acid is proline. In other embodiments, the amino acid is pyroglutamatic acid. In other embodiments, the amino acid is serine. In other embodiments, the amino acid is threonine. In other embodiments, the amino acid is tryptophan. In other embodiments, the amino acid is tyrosine. In other embodiments, the amino acid is valine.

In some embodiments, R$_2$ is alkyl. In other embodiments, R$_2$ is halide.

In some embodiments, R$_2$' is alkyl. In other embodiments, R$_2$' is halide.

In some embodiments, Q is O. In other embodiments, Q is alkyl. In other embodiments, Q is S. In other embodiments, Q is SO$_2$.

In some embodiments, R$_3$ is H. in other embodiments, R$_3$ is alkyl.

In some embodiments of the method, the at least one thyroid hormone analogue or thyroid hormone receptor agonist comprises a compound selected from the group consisting of

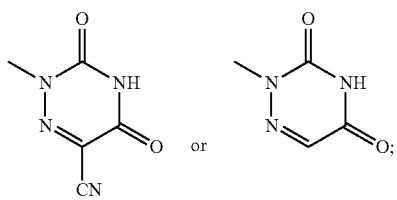

and
a compound represented by the structure of Formula II:

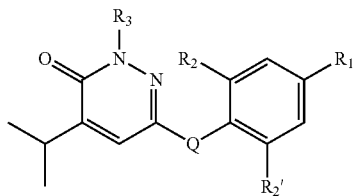

(Formula II)

wherein:

| $R^1$ | $R^2, R^{2'}$ | Q | $R^3$ |
|---|---|---|---|
| —CH$_2$CO$_2$H | CH$_3$, CH$_3$ | O | H |
| —CH$_2$CO$_2$H | CH$_3$, Cl | O | H |
| —CH$_2$CO$_2$H | Cl, Cl | O | H |
| —CH$_2$CO$_2$H | Br, Br | O | H |
| —CH$_2$CH$_2$CO$_2$H | Br, Br | O | H |
| —CH$_2$CO$_2$H | Cl, Cl | O | CH$_3$ |
| —NHCH$_2$CO$_2$H | Cl, Cl | O | H |
| —NHCOCO$_2$H | Cl, Cl | O | H |
| —CH$_2$CO$_2$H | Cl, Cl | —CH$_2$— | H |
| —CH$_2$CO$_2$H | Br, Br | —CH$_2$— | H |
| —CH$_2$CO$_2$H | Cl, Cl | S | H |
| —CH$_2$CO$_2$H | Cl, Cl | SO | H |
| —CH$_2$CO$_2$H | Cl, Cl | SO$_2$ | H |
| triazine-CN (N-methyl-6-oxo-5-cyano-1,2,4-triazin-3-yl) | Cl, Cl | O | H |
| triazine-CN | Cl, Cl | —CH$_2$— | H |
| triazine-CN | Cl, Cl | O | CH$_3$ |
| triazine (N-methyl-1,2,4-triazine-3,5-dione) | Cl, Cl | O | H |
| triazine | Cl, Cl | —CH$_2$— | H | or a pharmaceutically acceptable salts thereof, including mixtures thereof in all ratios and combination thereof.

In some embodiments of the method, the at least one thyroid hormone analogue or thyroid hormone receptor agonist is selected from the group consisting of 2-[3,5-dichloro-4-(5-isopropyl-6-oxo-1,6-dihydropyridazin-3-yloxy) phenyl]-3,5-dioxo-2,3,4,5-tetrahydro[1,2,4] triazine-6-carbonitrile (MGL-3196), 2-[4-[[4-Hydroxy-3-(1-methylethyl)phenyl]methyl]-3,5-dimethylphenoxy]acetic acid (GC1) and 2-((3,5-dimethyl-4-(4'-hydroxy-3'-isopropylbenzyl)phenoxy)methyl)-4-(3-chlorophenyl)-2-oxido(1,3,2)dioxaphosphonane (VK2809) or combinations thereof.

In some embodiments, the at least one thyroid hormone analogue or thyroid hormone receptor agonist comprises levothyroxine (L-thyroxine). In some such embodiments, the levothyroxine (L-thyroxine) comprises levothyroxine (L-thyroxine) sodium. In some embodiments, the at least one thyroid hormone analogue or thyroid hormone receptor agonist comprises dextrothyroxine. In some such embodiments, the dextrothyroxine comprises dextrothyroxine sodium. In some embodiments, the at least one thyroid hormone analogue or thyroid hormone receptor agonist comprises desiccated thyroid. In some embodiments, the at least one thyroid hormone analogue or thyroid hormone receptor agonist comprises thyroid extract. In some embodiments, the at least one thyroid hormone analogue or thyroid hormone receptor agonist comprises liothyronine. In some such embodiments, the liothyronine comprises liothyronine sodium. In some embodiments, the at least one thyroid hormone analogue or thyroid hormone receptor agonist comprises liotrix.

In some embodiments of the method, the at least one thyroid hormone analogue or thyroid hormone receptor agonist comprises MGL-3196.

In some embodiments of the method, the at least one fatty acid-bile acid conjugate comprises Aramchol™ and the at least one thyroid hormone analogue or thyroid hormone receptor agonist comprises MGL-3196.

In some embodiments of the method, co-administering the therapeutically effective amount of at least one fatty acid-bile acid conjugate; and at least one thyroid hormone analogue or thyroid hormone receptor agonist or salts thereof further comprises administering at least one pharmaceutically acceptable excipient.

In some embodiments of the method, co-administering the at least one fatty acid-bile acid conjugate and the at least one thyroid hormone analogue or thyroid hormone receptor agonist or salts thereof comprises co-administering a synergistically effective amount of the at least one fatty acid-bile acid conjugate and the at least one thyroid hormone analogue or thyroid hormone receptor agonist or salts thereof.

In some such embodiments, co-administering of said synergistically effective amount provides for at least one effect selected from the group consisting of:
a) a lower dose of at least one of the at least one fatty acid-bile acid conjugate or at least one thyroid hormone analogue or thyroid hormone receptor agonist;
b) a shorter treatment schedule; and
c) reduced incidence or severity of side-effects,
as compared to the effect obtained by administering a compound comprising the at least one fatty acid-bile acid conjugate or at least one thyroid hormone analogue or thyroid hormone receptor in the absence of the other compound.

In some embodiments of the method, the at least one fatty acid-bile acid conjugate comprises Aramchol™ and the at least one thyroid hormone analogue or thyroid hormone receptor agonist comprises MGL-3196, and the synergistically effective amount is at least one of from greater than 0 mg to less than 50 mg of MGL-3196 (such as about 0.2 mg, about 0.5 mg, about 1 mg, about 10 mg, about 20 mg, about 30 mg, about 40 mg or about 45 mg) and from greater than 0 mg to less than 400 mg of Aramchol™ (such as about 0.2 mg, about 0.5 mg, about 1 mg, about 10 mg, about 20 mg, about 30 mg, about 40 mg, about 50 mg, about 95 mg, about 100 mg, about 150 mg, about 200 mg, about 250 mg, about 300 mg, about 350 mg, or about 395 mg).

In some such embodiments, Aramchol™ is administered in an amount of from greater than 0 mg to less than 300 mg.

In some such embodiments, Aramchol™ is administered in an amount of from greater than 0 mg to less than 100 mg.

In some embodiments of the method, the liver disease is selected from the group consisting of non-alcoholic steatohepatitis (NASH), non-alcoholic fatty liver disease (NAFLD), emerging cirrhosis, non-cirrhotic hepatic fibrosis and liver fibrosis.

In some such embodiments, the liver fibrosis is associated with at least one condition selected from the group consisting of non-alcoholic fatty liver disease (NAFLD), non-alcoholic steatohepatitis (NASH) and emerging cirrhosis.

In some such embodiments, the liver fibrosis comprises non-cirrhotic hepatic fibrosis.

In some embodiments of the method, the subject has a disease or condition selected from the group consisting of, human immunodeficiency virus (HIV) infection, HIV and HCV co-infection, viral hepatitis, type 2 diabetes mellitus (T2DM), metabolic syndrome (MS), or a combination thereof.

In some such embodiments, the viral hepatitis is HBV or HCV infection.

In some embodiments of the method, co-administration comprises any one of: simultaneous administration, sequential administration, overlapping administration, concomitant administration, interval administration, continuous administration, contemporaneous administration or any combination thereof. In some such embodiments of the method, sequential co-administration is carried out in any order.

In some embodiments of the method, the fatty acid-bile acid conjugate is administered orally and the at least one thyroid hormone analogue or thyroid hormone receptor agonist is administered orally or parenterally, such as, for example, by intravenous administration, intraarterial administration, intramuscular administration, subcutaneous administration, intraosseous administration, intrathecal administration, or a combination thereof.

In some such embodiments, the fatty acid-bile acid conjugate is formulated as an orally administrable composition.

In some embodiments of the method, the fatty acid-bile acid conjugate is administered once per day.

In some embodiments of the method, the at least one thyroid hormone analogue or thyroid hormone receptor agonist is formulated as an orally administrable composition.

In some embodiments of the method, the fatty acid-bile acid conjugate and the at least one thyroid hormone analogue or thyroid hormone receptor agonist are provided in a single composition.

In some embodiments of the method, the at least one thyroid hormone analogue or thyroid hormone receptor agonist is administered once per day. In some embodiments, the at least one thyroid hormone analogue or thyroid hormone receptor agonist is administered twice per day, three times per day, four times per day, once per two days, once per three days, once per week or twice per week.

In some embodiments of the method, administration is carried out for one or more treatment cycles, such as one, two, three, four or more treatment cycles.

In some embodiments of the method, each treatment cycle comprises co-administration over a period of 1, 2, 3, 4, 5, 6,7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40 or more than 40 days. In some embodiments, a gap of one or more days, such as 1, 2, 3, 4, 5, 6, 7, 8, 9, 10, 11, 12, 13, 14 or more days is allowed between the completion of one treatment cycle and the beginning of a subsequent treatment cycle.

According to an aspect of some embodiments of the present invention, there is provide a kit comprising
(a) at least one individual dose of at least one fatty acid-bile acid conjugate; and
(b) at least one individual dose of at least one thyroid hormone analogue or thyroid hormone receptor agonist.

Unless otherwise defined, all technical and scientific terms used herein have the same meaning as commonly understood by one of ordinary skill in the art to which the invention pertains. In case of conflict, the specification, including definitions, will take precedence.

As used herein, the indefinite articles "a" and "an" mean "at least one" or "one or more" unless the context clearly dictates otherwise.

As used herein, when a numerical value is preceded by the term "about", the term "about" is intended to include all values having substantially the same effect, or providing substantially the same result, as the reference value. Thus, the range encompassed by the term "about" will vary depending on context in which the term is used, for instance the parameter that the reference value is associated with. Thus, depending on context, "about" can mean, for example, ±15%, ±10%, ±5%, ±4%, ±3%, ±2%, ±1%, or ±less than 1%.

As used herein, the term "pharmaceutically acceptable" refers to a material or method that can be used in medicine or pharmacy, including for human or veterinary purposes, for example, in administration to a subject.

As used herein, the terms "salt" and "pharmaceutically acceptable salt" include both acid and base addition salts.

As used herein, the term "acid addition salt" refers to those salts that retain the biological effectiveness and properties of the free bases, which are not biologically or otherwise undesirable, and which are formed with inorganic acids and organic acids.

As used herein, the term "base addition salt" refers to those salts that retain the biological effectiveness and properties of the free acids, which are not biologically or otherwise undesirable, and which are prepared from addition of an inorganic base or an organic base to the free acid.

As used herein, the term "pharmaceutical composition" refers to a formulation of one or more compounds or mixtures of the disclosure and a medium generally accepted in the art for the delivery of the biologically active compound to mammals, e.g., humans. Such a medium includes all pharmaceutically acceptable carriers, diluents or excipients therefor.

As used herein, the term "treating" includes ameliorating, mitigating, reducing worsening and reducing the instances of a disease or condition, or the symptoms of a disease or condition.

As used herein, the term "administering" includes any mode of administration, such as oral, subcutaneous, sublingual, transmucosal, parenteral, intravenous, intra-arterial, buccal, sublingual, topical, vaginal, rectal, ophthalmic, otic, nasal, inhaled, intramuscular, intraosseous, intrathecal, and transdermal, or a combination thereof "Administering" can also include providing a different compound that when ingested or delivered as above will necessarily transform into the compound that is desired to be administered, this type of "different compound" is often being referred to as a "prodrug". "Administering" can also include prescribing or filling a prescription for a dosage form comprising a particular compound. "Administering" can also include providing directions to carry out a method involving a particular compound or a dosage form comprising the compound or compounds.

As used herein, the term "therapeutically effective amount" means the amount of an active substance that, when administered to a subject for treating a disease, disorder, or other undesirable medical condition, is sufficient to have a beneficial effect with respect to that disease, disorder, or condition. The therapeutically effective amount will vary depending on the chemical identity and formulation form of the active substance, the disease or condition and its severity, and the age, weight, and other relevant characteristics of the patient to be treated. Determining the therapeutically effective amount of a given active substance is within the ordinary skill of the art and typically requires no more than routine experimentation.

As used herein, the term "liver disease" refers to any disturbance of liver function that causes illness. Liver disease is also referred to herein as "hepatic disease".

It should be understood that the text of every journal article, patent, patent application, publication, and the like that is mentioned herein is intended to be included in this application to the extent that is relevant to the purpose of the citation. All numerical ranges should be understood to include each and every numerical point within the numerical range and should be interpreted as reciting each and every numerical point individually. The endpoints of all ranges directed to the same component or property are inclusive and intended to be independently combinable.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

EXAMPLES

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1

A double-blind, placebo-controlled randomized trial is designed to evaluate the safety and efficacy of co-administration of Aramchol™ in combination with MGL-3196 in subjects of age 18 to 75 years with Non-Alchoholic Steatohapatitis (NASH), confirmed by liver biopsy performed in a period of 6 months before entering the study.

Inclusion Criteria

Male or female age 18 to 75 years.

BMI between 25 kg/m2 to 40 kg/m2 or waist circumference between 88 cm to 200 cm for women, and between 102 cm to 200 cm for men.

Known type II Diabetes Mellitus or pre-Diabetes according to American Diabetes Association. One of the following 3 criteria is needed for pre-Diabetes: Fasting Plasma Glucose >100 mg/dl (5.5 mmol/1) or 2 hPG following 75 g OGTT>140 (7.8 mmol/1) mg/dl or HbA1c>5.7%.

Histologically proven Steatohepatitis on a diagnostic liver biopsy performed either during screening or within 6 months before screening visit, confirmed by central laboratory reading of the slides. (Steatosis.gtoreq.1+inflammation.gtoreq.1+ballooning.gtoreq.1). Total activity NAS score of 4 or more.

Liver fat concentration in the liver of 5.5% or more as measured by NMRS.

Biopsies with an activity NAS score of 4 or more.

Normal synthetic liver function (serum albumin >3.2 g/dl, INR 0.8-1.2, conjugated bilirubin <35 .mu.mol/L).

Understanding the nature of the study and signature of the written informed consent.

Negative pregnancy test at study entry for females of child bearing potential.

Females of child bearing potential practicing reliable contraception throughout the study period (including oral contraceptives) as well as negative pregnancy test at study entry.

Hypertensive patients are well controlled by stable dose of anti-hypertensive medication for at least 2 months prior to screening.

Patients previously treated with vitamin E (>400 IU/day), Polyunsaturated fatty acid (>2 g/day) or Ursodeoxycholic acid or fish oil are included if stopped or at least maintained on stable dose at least 3 months prior to diagnostic liver biopsy (and are not started during the trial). These treatments-dosages are allowed if they were stable for at least 12 months prior to biopsy and can remain stable throughout the study.

For patients with type II Diabetes, glycaemia must be controlled (Glycosylated Hemoglobin Alc.ltoreq.9%) while any HbA1c change should not exceed 1.5% during 6 months prior to enrolment). Treatments with anti-diabetic medications (except for those mentioned in Exclusion 16) are permitted if glycaemia is self-monitored by the patient. HbA1c can be repeated at Investigator's discretion.

Exclusion Criteria

Patients with other active (acute or chronic) liver disease other than NASH (e.g. viral hepatitis, unless eradicated at least 3 years prior to screening; genetic hemochromatosis; Wilson disease; alpha lantitripsin deficiency; alcohol liver disease; drug-induced liver disease) at the time of randomization.

Patients with clinically or histologically documented liver cirrhosis

Known alcohol and/or any other drug abuse or dependence in the last five years.

Known history or presence of clinically significant cardiovascular, gastrointestinal, metabolic other than Diabetes Mellitus, neurologic, pulmonary, endocrine, psychiatric, neoplastic disorder or nephrotic syndrome, that in the opinion of the Investigator warrant exclusion from the study.

Patients with familial (i.e., genetic) hypertriglyceridemia and familial (i.e., genetic) hypercholesterolemia.

History or presence of any disease or condition known to interfere with the absorption distribution, metabolism or excretion of drugs including bile salt metabolites (e.g. inflammatory bowel disease (IBD)), previous intestinal (ileal or colonic) operation, chronic pancreatitis, celiac disease or previous vagotomy. Ongoing Chronic constipation Patients with heart or brain pacemaker (i.e., implantable neurological devices).

Surgery during the last three month before screening which involve stent implantation of metal devices (e.g. knee, hip etc.)

Weight loss of more than 5% within 6 months prior to randomization.

History of bariatric surgery within 5 years of liver biopsy.

Uncontrolled arterial hypertension.

Women who are pregnant and breast feeding.

Diabetes Mellitus other than type II (type I, endocrinopathy, genetic syndromes etc.).

Patients with HIV infection.

Daily alcohol intake >20 g/day for women and >30 g/day for men (on average per day) as per medical history.

Treatment with other anti-diabetic medications: GLP-1 receptor agonists and Thiazolidinediones (TZDs), unless started at least 12 months prior to biopsy and on stable dose for 6 months. In case of GLP-1 receptor agonists stopped, it should be at least 6 months before biopsy as per medical history.

SGLT-2 Inhibitors, Metformin, fibrates, statins, insulin, DPP-4 inhibitors and sulfonylurea unless prescribed dose has been stable for the last 6 months prior to the biopsy.

Treatment with Valproic acid, Tamoxifen, Methotrexate, Amiodarone or chronic treatment with anti-cholinergic agents, corticosteroids, high dose estrogen and tetracycline within 12 months prior to the screening visit.

Chronic treatment with antibiotics (e.g. Rifaximin).

Homeopathic and/or alternative treatments. Any treatment is stopped during the screening period at least 48 hours before randomization.

Uncontrolled hypothyroidism defined as Thyroid Stimulating hormone >2.times. the upper limit of normal (ULN). Thyroid dysfunction controlled for at least 6 months prior to screening is permitted.

Patients with renal dysfunction eGFR <40.

Unexplained serum creatine phosphokinase (CPK) >3.times. the upper limit of normal (UNL). Patients with a reason for CPK elevation may have the measurement repeated prior to randomization; a CPK retest >3.times. ULN leads to exclusion.

Patients with condition(s) that makes them unsuitable to perform the NMRS (as determined by the PI or the MRI facility).

Hypersensitivity to Aramchol or to any of the excipients in the tablets

Hypersensitivity to cholic acid or bile acid sequestrants

Intervention

Subjects are administered tablets according to the protocol of Table 1 orally in the morning within 30 min after breakfast with a glass of water (250 ml).

Subjects are allowed to omit study drugs up to 3 consecutive days during the study.

Further details of inclusion and exclusion criteria and protocol for such a trial are provided in U.S Publication No. 20180125862, which is incorporated by reference as if fully set out herein.

Briefly, subjects are administered Aramchol, MGL-3196 and placebo in tablet form, according to the table below. Study Arms:

TABLE 1

| Intervention | Aramchol (mg/day) | MGL-3196 (mg/day) | Placebo |
|---|---|---|---|
| Arm 1 - Negative control | 0 | 0 | One placebo tablet matching Aramchol ™ and one placebo tablet matching MGL-3196 |
| Arm 2 - Positive Control (a) | 400 | 0 | — |
| Arm 3 - Positive Control (b) | 0 | 50 | — |
| Arm 4 - Experimental (Known Doses) | 400 | 50 | — |
| Arm 5 - Experimental (low MGL Dose) | 400 | 35 | — |
| Arm 6 - Experimental (low MGL Dose) | 400 | 25 | — |
| Arm 7 - Experimental (low MGL Dose) | 400 | 10 | — |
| Arm 8 - Experimental (low Aramchol Doses) | 350 | 50 | — |
| Arm 9 - Experimental (low Aramchol Dose) | 250 | 50 | — |
| Arm 10 - Experimental (low Aramchol Dose) | 150 | 50 | — |

Study arm 1 (Negative control): One placebo tablet matching Aramcol™ and one placebo tablet matching MGL-3196;

Study arm 2 (Positive control): One tablet of Aramchol™ 400 mg and one placebo tablet matching MGL-3196;

Study arm 3 (Positive control): One placebo tablet matching Aramchol™ 400 mg and one tablet of MGL-3196 50 mg;

Study arm 4 (Known doses): One tablet of Aramchol™ 400 mg and one tablet of MGL-3196 50 mg;

Study arm 5 (Low dose MGL-3196): One tablet of Aramchol™ 400 mg and one tablet of MGL-3196 35 mg;

Study arm 6 (Low dose MGL-3196): One tablet of Aramchol™ 400 mg and one tablet of MGL-3196 25 mg;

Study arm 7 (Low dose MGL-3196): One tablet of Aramchol™ 400 mg and one tablet of MGL-3196 10 mg;

Study arm 8 (Low dose Aramchol™): One tablet of Aramchol™ 350 mg and one tablet of MGL-3196 50 mg;

Study arm 9 (Low dose Aramchol™): One tablet of Aramchol™ 250 mg and one tablet of MGL-3196 50 mg;

Study arm 10 (Low dose Aramchol™): One tablet of Aramchol™ 150 mg and one tablet of MGL-3196 50 mg.

Results

Treatment with a combination of Aramchol™ 400 mg and MGL-3196 50 mg (Experimental Arm 4) results in one or more of the following effects compared to treatment with Aramchol™ 400 mg in the absence of MGL-3196 (Experimental Arm 2) and MGL-3196 50 mg in the absence of Aramchol™ (Experimental Arm 3):

reduced liver triglycerides ratio reduced Hepatic triglycerides and improved insulin sensitivity and lower glucose level statistically significant increase in the proportion of subjects with reduced fibrosis statistically significant increase in the proportion of subjects with NAS Score improvement statistically significant increase in the proportion of subjects with improved SAF Activity scores statistically significant increase in the proportion of subjects with NASH resolution reducing or preventing worsening, or improving of the subject's liver fibrosis score reduction of at least ~20% in the level of pro-hormone, free thyroxine (free T4).

statistically significant reduction of LDL cholesterol; non-high-density lipoprotein cholesterol increased testosterone increased sex hormone-binding globulin (SHBG).

Treatment with Aramchol™ 400 mg in combination with MGL-3196 at less than 50 mg (Arms 5 to 7) shows at least one or more of the following improvements compared to monotherapy with Aramchol™ 400 mg in the absence of MGL-3196 (Arm 2) and MGL-3196 50 mg (Arm 3) in the absence of Aramchol™:

equivalent efficacy compared to MGL-3196 50 mg monotherapy (Arm 3)

reduced side effect profile compared to MGL-3196 50 mg monotherapy (Arm 3).

Treatment with less than Aramchol™ 400 mg in combination with MGL-3196 50 mg (Arms 8 to 10) shows at least one or more of the following improvements compared to monotherapy with Aramchol 400 mg (Arm 2) in the absence of MGL-3196 and MGL-3196 50 mg (Arm 3) in the absence of Aramchol™:

equivalent efficacy compared to Aramchol™ 400 mg monotherapy (Arm 2)

reduced side effect profile compared to Aramchol™ 400 mg monotherapy (Arm 2).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and scope of the appended claims.

Citation or identification of any reference in this application shall not be construed as an admission that such reference is available as prior art to the invention.

What is claimed is:

1. A therapeutic combination comprising a therapeutically effective amount of aramchol, or a pharmaceutically acceptable salt thereof, and a therapeutically effective amount of MGL-3196, or a pharmaceutically acceptable salt thereof, and a carrier.

2. The therapeutic combination according to claim 1, wherein the amount of Aramchol™ is greater than 0mg and less than 400 mg, and the amount of MGL-3196 is greater than 0 mg and less than 50 mg.

3. A method of treating, stabilizing or lessening the severity or progression of a liver disease, comprising co-administrating to a subject in need thereof a therapeutically effective amount of aramchol; and MGL-3196 or salts thereof.

4. The method according to claim 3, wherein the amount of Aramchol™ is greater than 0mg and less than 400 mg, and the amount of MGL-3196 is greater than 0 mg and less than 50 mg.

5. The method according to claim 3, wherein said treating, stabilizing or lessening the severity or progression of a liver disease comprises at least one therapeutic effect selected from the group consisting of:

a) a lower dose of aramchol or the MGL-3196;

b) a shorter treatment schedule; and c) reduced incidence or severity of side-effects, as compared to the effect obtainable by administration of aramchol or MGL-3196 in the absence of the other compound.

6. The method according to claim 3, wherein said liver disease is selected from the group consisting of non-alcoholic steatohepatitis (NASH), non-alcoholic fatty liver disease (NAFLD), emerging cirrhosis, non-cirrhotic hepatic fibrosis and liver fibrosis.

7. The method according to claim 3, wherein said subject has a disease or condition selected from the group consisting of human immunodeficiency virus (HIV) infection, HIV and HCV co-infection, viral hepatitis, type 2 diabetes mellitus (T2DM), metabolic syndrome (MS), or a combination thereof.

8. The method according to claim 3, wherein said co-administrating to a subject in need thereof of aramchol; and MGL-3196 or salts thereof further comprises administering at least one pharmaceutically acceptable excipient.

9. The method according to claim 3, wherein said co-administration comprises any one of: simultaneous administration, sequential administration, overlapping administration, concomitant administration, interval administration, continuous administration, contemporaneous administration or any combination thereof. In some such embodiments of the method, sequential co-administration is carried out in any order.

10. The method according to claim 3, wherein said aramchol is administered orally and said MGL-3196 is administered orally or parentally.

11. The method according to claim 3, wherein said aramchol is administered once per day.

12. The method according to claim 3, wherein said aramchol and said MGL-3196 are provided in a single composition.

13. The method according to claim 3, wherein said MGL-3196 is administered once per day.

14. The method according to claim 3, wherein said MGL-3196 is administered twice per day, three times per day, four times per day, once per two days, once per three days, once per week or twice per week.

15. The method according to claim 3, wherein said administration is carried out for one or more treatment cycles, such as one, two, three, four or more treatment cycles.

16. A kit comprising (a) aramchol; and (b) MGL-3196.

* * * * *